United States Patent [19]

Shoesmith, deceased et al.

[11] Patent Number: Plant 7,683

[45] Date of Patent: Oct. 22, 1991

[54] CHRYSANTHEMUM PLANT NAMED DAYTONA

[75] Inventors: Leonard H. Shoesmith, deceased, late of Woking, England, by May V. Shoesmith, executrix; May V. Shoesmith, Woking, England; Peter S. Hesse, Nipoma, Calif.

[73] Assignee: Yoder Brothers, Inc., Barberton, Ohio

[21] Appl. No.: 562,380

[22] Filed: Aug. 3, 1990

[51] Int. Cl.[5] ..... A01H 5/00

[52] U.S. Cl. ..... Plt./76

[58] Field of Search ..... Plt./74, 74.1, 76, 80

*Primary Examiner*—Howard J. Locker

*Attorney, Agent, or Firm*—Foley & Lardner

[57] ABSTRACT

A Chrysanthemum plant named Daytona particularly characterized by its flat capitulum form; spider capitulum type; light purple ray floret color; diameter across face of capitulum of 18 to 19.5 cm. when grown as a disbud, and 12 to 14 cm. when grown as a spray cut mum; flowering response in various locations in the United States and Canada under normal temperature ranges from 57 to 68 days after start of short days; flowering response in Bogota under minimum 6.3° C. night and maximum 30.9° C. day is 68 days after start of short days; peduncle length of first lateral in the United States and Canada ranges from 8 to 15 cm., the fourth lateral from 13 to 23 cm. on open, terminal sprays; plant height when grown as a single stem cut mum in Parrish, Fla., with 19 to 25 long days prior to start of short days is 119 to 140 cm.; when grown in Bogota, Colombia with 14 long days prior to start of short days is 124 cm.; and good tolerance to low temperatures for bud initiation and flower development.

3 Drawing Sheets

1

The present invention comprises a new and distinct cultivar of Chrysanthemum, botanically known as *Dendranthema grandiflora,* and referred to by the cultivar name Daytona.

Daytona, identified as SP79-1760-PS, was originated from a cross made by Leonard H. Shoesmith and May Victoria Shoesmith in a controlled breeding program in Westfield-Woking, England, in 1978.

Both the female and the male parents of Daytona were unknown seedlings from Shoesmith breeding lines.

Daytona was discovered and selected as one flowering plant within the progeny of the stated cross by Peter S. Hesse in November 1979, in a controlled environment in West Chicago, Ill.

The first act of asexual reproduction of Daytona was accomplished when vegetative cuttings were taken from the initial selection in January 1980 in a controlled environment in West Chicago, Ill., by technicians working under the supervision of Peter S. Hesse.

Horticultural examination of controlled flowerings of successive plantings has shown that the unique combination of characteristics as herein disclosed for Daytona are firmly fixed and are retained through successive generations of asexual reproduction.

Daytona has not been observed under all possible environmental conditions. The phenotype may vary significantly with variations in environment such as temperature, light intensity and daylength. For example, plant height will increase with an increased number of long days after planting prior to start of short days. Under low night temperatures (10 degrees Celsius and lower) flowering can be expected to be delayed. Under high temperatures (25 degrees Celsius night and 35 degrees Celsius day) flowering can be expected to be delayed and also be more uneven than under normal temperatures. Normal temperatures can be described as 15 degrees Celsius minimum night and 25 degrees Celsius maximum day.

2

The following observations, measurements and comparisons describe plants grown at various locations in the United States and Canada, including Parrish, Fla.; Encinitas, Calif.; Strathroy, Ontario, Canada; and in Bogota, Colombia under greenhouse conditions which approximate those generally used in commercial greenhouse practice. The low temperature tolerance was determined in the April 1990 trial flowering in Bogota, Columbia.

The following traits have been repeatedly observed and are determined to be basic characteristics of Daytona, which, in combination, distinguish this Chrysanthemum as a new and distinct cultivar:

1. Flat capitulum form.
2. Spider capitulum type.
3. Light purple ray floret color.
4. Daytona can be grown both as a disbud and as a natural spray cut mum.
5. Diameter across face of capitulum when grown as a disbud of 18 to 19.5 cm. when fully opened; diameter when grown as a spray mum of 12 to 14 cm. when fully opened.
6. Flowering response ranges from 57 to 68 days after start of short days when grown in the United States and Canada. Flowering response in Bogota, Colombia under minimum 6.3° C. night temperature and maximum 30.9° C. day temperature is 68 days after start of short days, when flowered in April 1990.
7. Peduncle length of the first lateral at flowering after removing the apical bud without growth regulator applications is 8 to 15 cm. when grown in the United States and Canada, and 10 cm. when grown in Bogota, Colombia. Peduncle length of the fourth lateral at flowering is 13 to 23 cm. when grown in the United States and Canada, and 15 cm. when grown in Bogota when flowered in April 1990.
8. Plant height when grown as a single stem cut mum when grown in Parrish, Fla. with 19 to 25 long days prior to start of short days, is 119 to 140 cm.; when grown in Bogota, with 14 long days prior to start of short days, plant height is 124 cm.

9. Good tolerance to night temperatures as low as 5°-10° C. for bud initiation and flower development. Average minimum low night temperatures in our Bogota trials ranged from 6.3° C. to 10.0° C.

The accompanying photographic drawings show typical inflorescence and leaf characteristics of Daytona, with the colors being as nearly true as possible with illustrations of this type.

Sheet 1 is a color photograph of two plants of Daytona, the one on the left being grown as a single stem cut spray mum, and the one on the right being grown as a disbud cut mum.

Sheet 2 is a black and white photograph of three views of the inflorescence of Daytona.

Sheet 3 is a black and white photograph showing the upper and under sides of the leaves of Daytona at three stages of development (mature, intermediate and immature).

Of the commercial cultivars known to the inventors, the most similar in comparison to Daytona is the cultivar identified as Pirouette, a pale lavender pink flat spider cut spray mum, disclosed in U.S. Plant Pat. No. 6,157. Reference is made to attached Chart A, which compares certain characteristics of Daytona to the same characteristics of Pirouette.

Similar traits are ray floret color, capitulum form and type, and spray formation. The peduncle length of both cultivars is comparable. Daytona has a larger diameter of capitulum, and a slightly earlier response by 2 to 3 days than Pirouette. Daytona has been tested in Bogota only once, in April 1990, while Pirouette has not been tested in Bogota.

In the following description color references are made to The Royal Horticultural Society Colour Chart. The color values were determined on plant material grown in Salinas, Calif. on Dec. 11, 1989.

Classification:

*Botanical.*—*Dendranthema grandiflora* cv. Daytona.

*Commercial.*—Spider cut disbud and spray mum.

INFLORESCENCE

A. Capitulum:

*Form.*—Flat.

*Type.*—Spider.

*Diameter across face.*—As disbud, 18 to 19.5 cm.; as spray 12 to 14 cm.

B. Corolla of ray florets:

*Color (general tonality from a distance of three meters).*—Purple.

*Color.*—Spoons: Inner ray florets, 78B to 78C; outer ray florets, 78C to 78D. Tubes: 75C to 75D.

*Shape.*—Straight, tubular, with small open spoon at petal tip.

C. Corolla of disc florets:

*Color (mature).*—Closest to 14A.

*Color (immature).*—Closest to 144A.

D. Reproductive organs:

*Androecium.*—Present on disc florets only; very few disc florets, barely visible in the mature flower; scant pollen.

*Gynoecium.*—Present on both ray and disc florets.

PLANT

A. General appearance:

*Height.*—Plant height when grown as a single stem cut mum in Parrish with 19 to 25 long days prior to start of short days is 119 to 140 cm.; when grown in Bogota with 14 long days prior to start of short days, plant height is 124 cm.

B. Foliage:

*Color (upper surface).*—147A.

*Color (under surface).*—147B.

*Shape.*—See photograph.

CHART A

COMPARISON OF DAYTONA AND PIROUETTE

| CHARACTERISTIC | DAYTONA | PIROUETTE |
|---|---|---|
| Ray floret color | Light purple (75C-75D) tubes with darker purple spoons | Same as Daytona 75C-75D |
| Capitulum form and type | Flat/spider | Flat/spider |
| Spray formation | Terminal | Terminal |
| Peduncle length: | | |
| 1st lateral, U.S. & Canada | 8 to 15 cm. | 10 to 15 cm. |
| 4th lateral, U.S. & Canada | 13 to 23 cm. | 18 to 23 cm. |
| 1st lateral, Bogota (1 test) | 10 cm. | Not tested |
| 4th lateral, Bogota (1 test) | 15 cm. | Not tested |
| Diameter across face of capitulum as disbud: | 18 to 19.5 cm. | Not available |
| as spray: | 12 to 14 cm. | 8 to 12 cm. |
| Plant height: | | |
| 19-25 long days, Parrish, Fl. | 130 to 135 mm. | 119 to 140 cm. |
| 14 long days, Bogota | 124 cm. | Not tested |
| Flowering response period | | |
| United States and Canada | 57 to 68 days | 60 to 70 days |
| Bogota | 68 days | Not tested |
| Low night temperature tolerance: | Good | Not tested |

COMPARISONS MADE OF PLANTS GROWN AS SINGLE STEM SPRAY CUT MUMS IN VARIOUS LOCATIONS IN THE UNITED STATES AND CANADA, AND IN BOGOTA, COLOMBIA

We claim:

1. A new and distinct Chrysanthemum plant named Daytona, as described and illustrated.

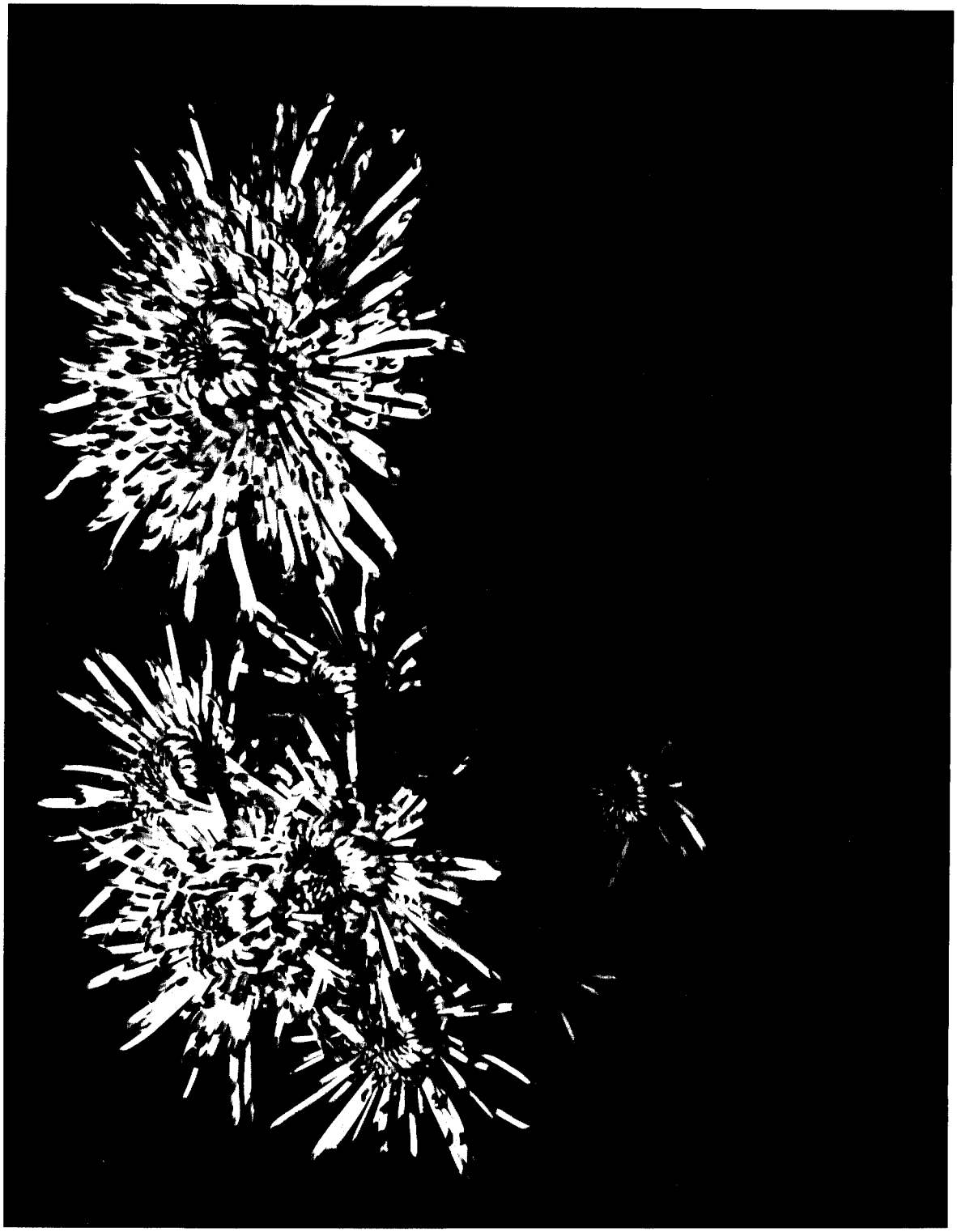

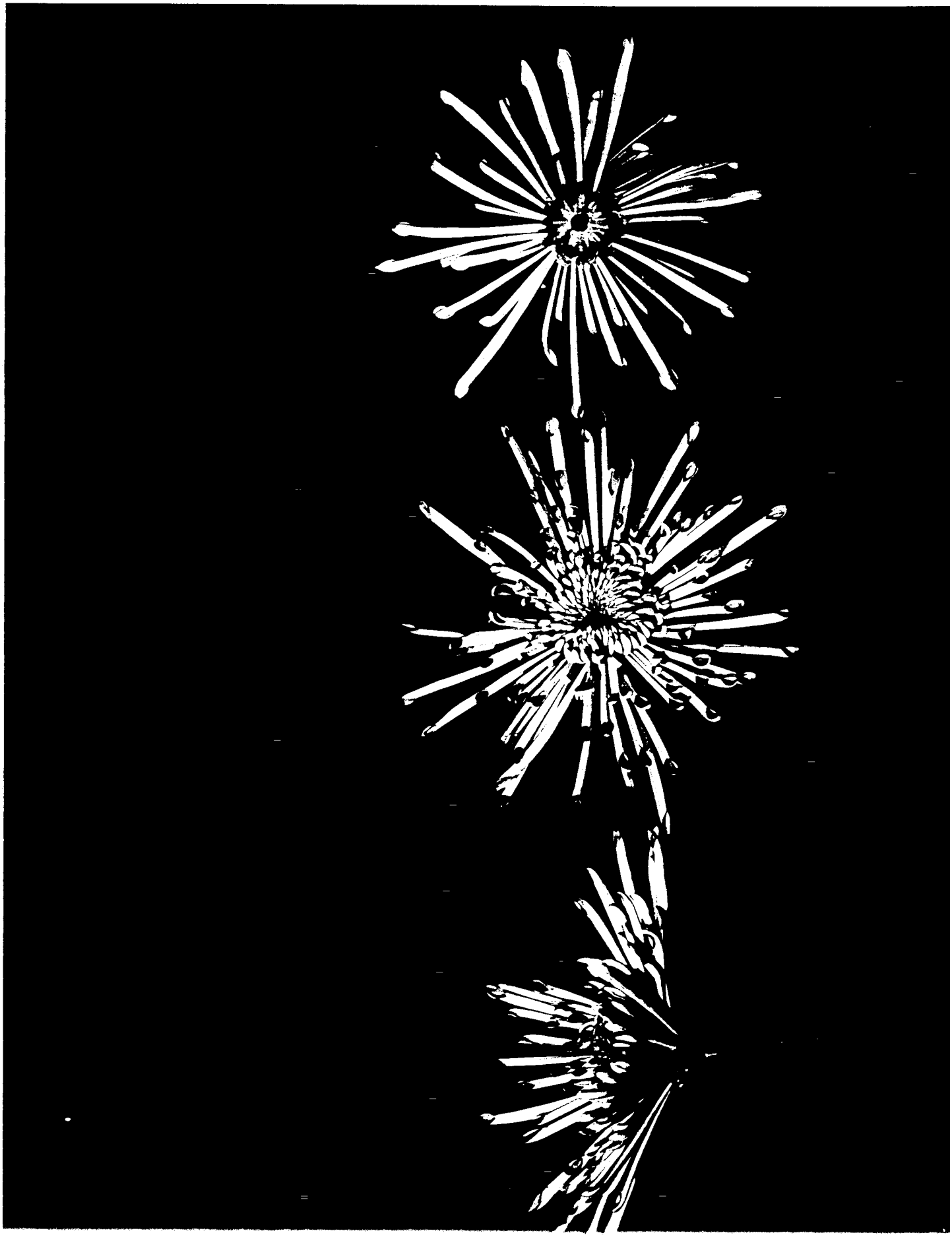

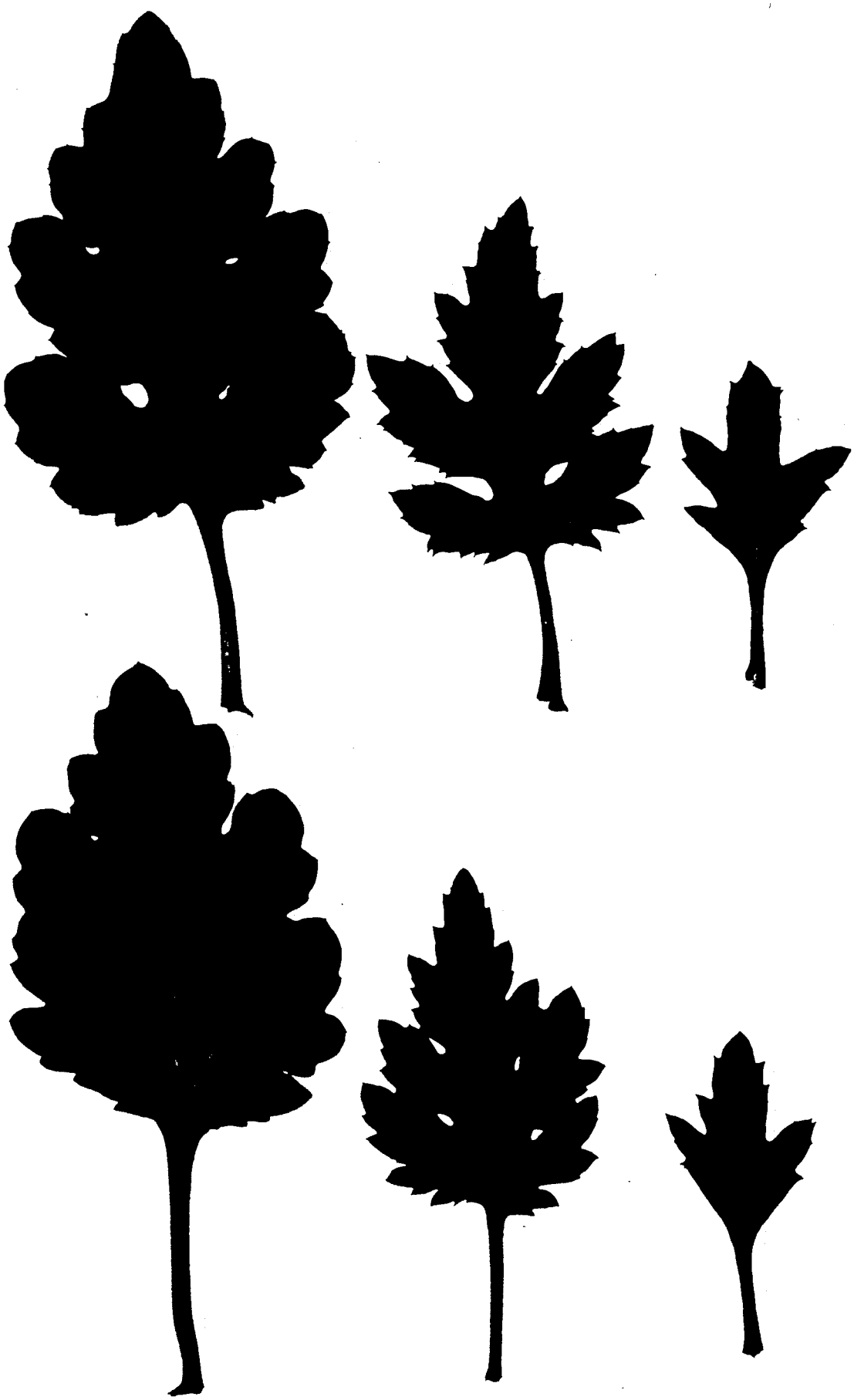

* * * * *